United States Patent [19]
Johnson et al.

[11] Patent Number: 4,946,133
[45] Date of Patent: Aug. 7, 1990

[54] HEMOSTASIS VALVE

[75] Inventors: Wade M. Johnson, Minneapolis; Edward A. Barlow, Bloomington, both of Minn.

[73] Assignee: Schneider (U.S.A.) Inc., A Pfizer Co., Plymouth, Minn.

[21] Appl. No.: 274,479

[22] Filed: Nov. 21, 1988

[51] Int. Cl.⁵ .............................................. F16L 37/28
[52] U.S. Cl. .................................. 251/149.1; 604/256; 604/905; 137/844
[58] Field of Search ................................ 604/905, 256; 251/149.1; 137/844

[56] References Cited

U.S. PATENT DOCUMENTS

| | | | |
|---|---|---|---|
| 1,189,624 | 7/1916 | Rohrbacher | 251/149.1 |
| 3,837,381 | 9/1974 | Arroyo | 251/149.1 |
| 4,143,853 | 3/1979 | Abramson | 251/149.1 |
| 4,436,519 | 3/1984 | O'Neill | 604/256 |
| 4,765,588 | 8/1988 | Atkinson | 251/149.1 |

Primary Examiner—A. Michael Chambers
Attorney, Agent, or Firm—Haugen and Nikolai

[57] ABSTRACT

The hemostasis valve gasket for use in an introducer which is integrally formed from an elastomeric material so as to exhibit resiliency and which is designed to close about small diameter objects such as a guide wire and about larger diameter objects such as a working catheter or guide catheter to prevent air or blood leakage. The gasket includes a cylindrical base with a central bore therethrough and a hollow convex domed shaped member projecting therefrom. The hollow dome shaped member terminates in a concave section. The concave section of the dome shaped member has at least one arcuate slit formed in the external surface which extends inwardly toward the hollow chamber to form a central, self-sealing passage aligned with the central bore of the cylindrical base member.

4 Claims, 3 Drawing Sheets

HEMOSTASIS VALVE

BACKGROUND OF THE INVENTION

This invention relates to a hemostasis valve used in conjunction with a cannula or introducer to position and manipulate intravascular catheters. Such catheters are typically used in angiography or angioplasty procedures. Angiography is a well known and very valuable procedure used in the diagnosis of vascular and organ disease. Angioplasty has, in recent years, come into its own as a viable method for treating blockages in the coronary arteries. Both of these procedures involve the introduction of a hollow tubular catheter into one of the major arteries or veins. The catheter is then advanced and maneuvered into smaller branching vessels.

Prior art techniques for introducing such catheters included a "cut down" method. This method involves introducing the catheter directly through a surgical incision made in the vein or artery. This method is unsatisfactory because it inevitably involves loss of blood through the incision. The use of this procedure also requires, in nearly all instances, venus ligation and arterial repair.

More recently, physicians have adopted an alternative procedure which includes placing a percutaneous sheath known as an introducer into the lumen of the blood vessel. The guide wires and catheters to be used are then inserted into the blood vessel through the introducer.

Two recognized problems with this latter technique are excess bleeding and the possible creation of air embolisms during the insertion, removal or manipulation of the catheter. Attempts have been made to solve these problems by developing a suitable hemostasis valve or gasket for use in conjunction with the introducer. For example, U.S. Pat. No. 4,000,739 issued on Jan. 4, 1977 to Robert C. Stevens discloses such a gasket system. This system involves the use of two disk-like gaskets. The first gasket has a round hole and the second has a Y-shaped slit. These gaskets are intended to cooperate to close the passage of the introducer during catheter changes.

U.S. Pat. No. 4,436,519, issued on Mar. 13, 1984 to William J. O'Neil, discloses a dome-shaped hemostasis valve. This valve seats in the lumen of an introducer. The valve is intended to seal the lumen to inhibit blood loss through the lumen. This valve includes a body having a central passage and a resilient dome-shaped diaphragm having a wall member with a single linear slit. A dome-shaped diaphragm is used because, according to the '519 Patent, it will act in cooperation with the walls of central passage to resiliently urge the slit closed when no catheter is present therethrough.

Still another valve arrangement is disclosed in U.S. Pat. No. 4,626,245 to Weinstein. This patent discloses an elastomeric partition valve of one piece construction. The valve includes a first slit defined by one side of the partition valve and a second slit defined by the opposite side. Each slit has a location which creates two spaced apart points of intersection with the other slit. The Weinstein Patent further indicates that the first and second slit should both have a Y-shape.

While each of the designs discussed above have certain advantages, none of them are deemed to be fully satisfactory. For example, each permits a certain amount of blood leakage. They do not provide a sufficiently tight seal when only the guide wire is in place. This is particularly true for smaller diameter guide wires.

SUMMARY OF THE INVENTION

It is therefore an objection of the present invention to provide a hemostasis valve gasket used in conjunction with an introducer during an angioplasty or angiographic procedure which will greatly inhibit or prevent blood leakage through the valve during the procedure. More specifically, the object of the present invention is to provide a hemostasis valve which will (a) seal around any suitably sized guide wire, (b) seal around any size catheter, and (c) provide very low resistance to passing the guide wire or catheter through the valve.

The present invention achieves these objectives by providing a valve having a cylindrical base and dome-shaped member which terminates in a concaved central section. The base includes an opening through its center through which the guide wire and catheter can be passed. The concave surface of the dome includes one or more radial slits. The slits may or may not pass completely through the material at the center of its concaved central section. If they do not pass through the center, the remainder of the material is punctured using a guide wire to create a passageway. The remaining portions of the slit are utilized to permit blood pressure to collapse the dome about the penetrating guide wire or catheter to improve the quality of the seal.

DETAILED DESCRIPTION OF THE PREFERRED EMBODIMENT

Figure 3:
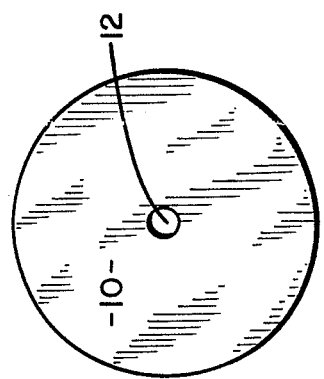
FIG. 3 is a plain view of the distal end valve gasket of the present invention.
Figure 2:
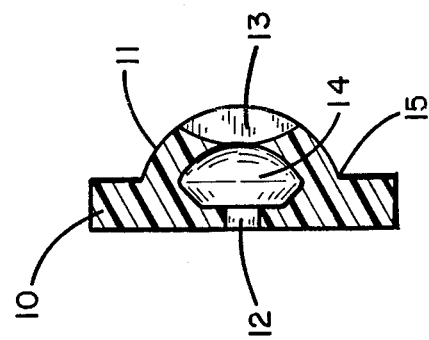
FIG. 2 is a cross sectional view through line 2—2 of FIG. 1.
Figure 1:
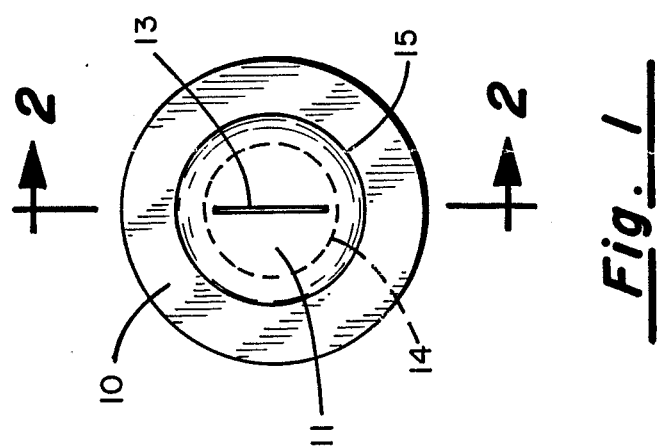
FIG. 1 is a plan side view of the proximal end of the valve gasket of the present invention.

The valve gasket of the present invention is preferably made of an elastomeric material such as natural rubber or silicone rubber. The valve gasket is comprised of a distal flange member 10 and a proximal dome member 11. The distal member 10 is, essentially, cylindrical in shape. It has a central circular opening 12 extending through its thickness dimension and through which a catheter and/or a guide wire can be inserted. The proximal dome member 11 has a dome shape in which is found an arcuate narrow slit. Within the proximal dome member 11 is a hollow cavity 14.

The proximal dome member 11 projects out from the distal section 10 as shown. The diameter of base 15 of the dome member 11 is sized to encompass approximately ½ to ¾ of the diameter of the cylindrical distal flange member 10. The hollow cavity 14 within the dome member and the arcuate slit 13 are designed so that a very thin membrane of material (in the range of 2 to 3 mil) exists between cavity 14 and slit 13 along a common tangent in the centermost section of the dome member 11. The membrane created by the slit 13 is easily ruptured upon the introduction of a guide wire allowing it to pass through the dome section.

This opening, however, is very small. Its width and length is much, much smaller than the overall length of the slit 13. The slit 13 is made much longer than the opening through the dome to provide a means by which blood pressure can apply sufficient force against the material of the dome to close the opening when no implements are present in the opening. The slit also permits blood pressure to seal the valve about any suitable catheter or guide wire when present in the opening.

Figure 4:
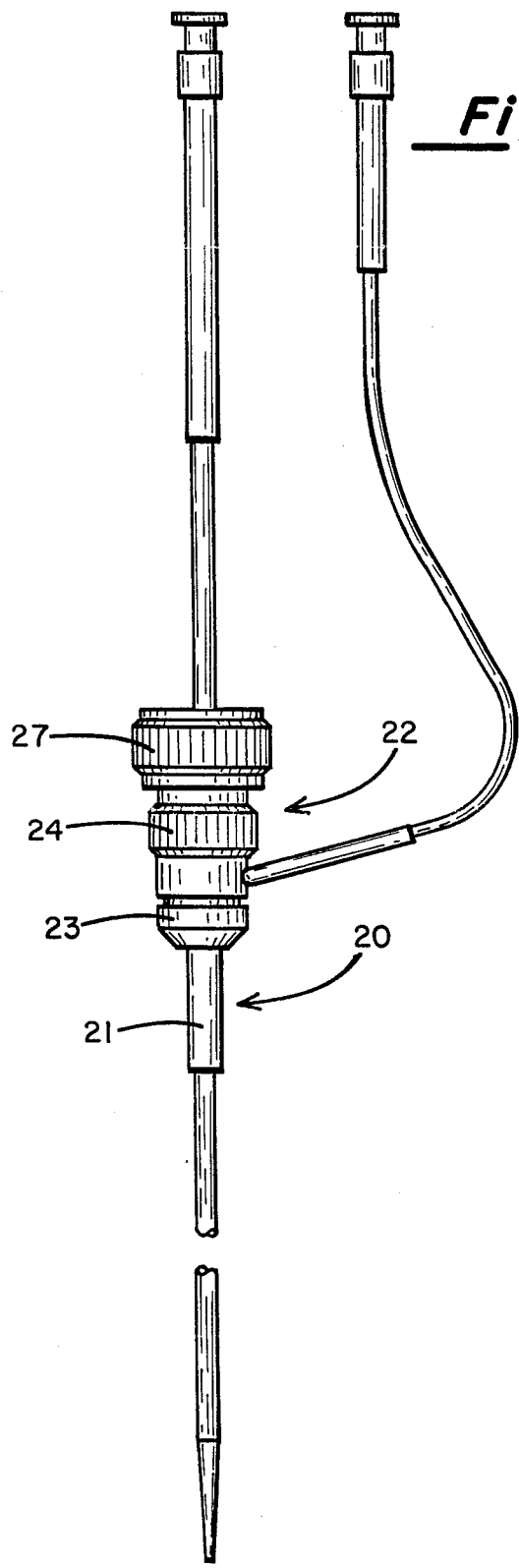
FIG. 4 is a plain view of a conventional introducer.
Figure 5:
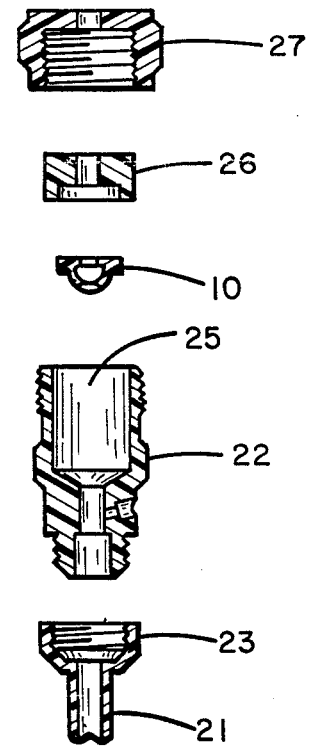
FIG. 5 is an exploded view of a portion of a conventional introducer which retains the valve of the present invention.

When in use, the valve is inserted into and retained in position by cooperating parts of a conventional introducer shown in FIGS. 4 and 5.

Figure 6:
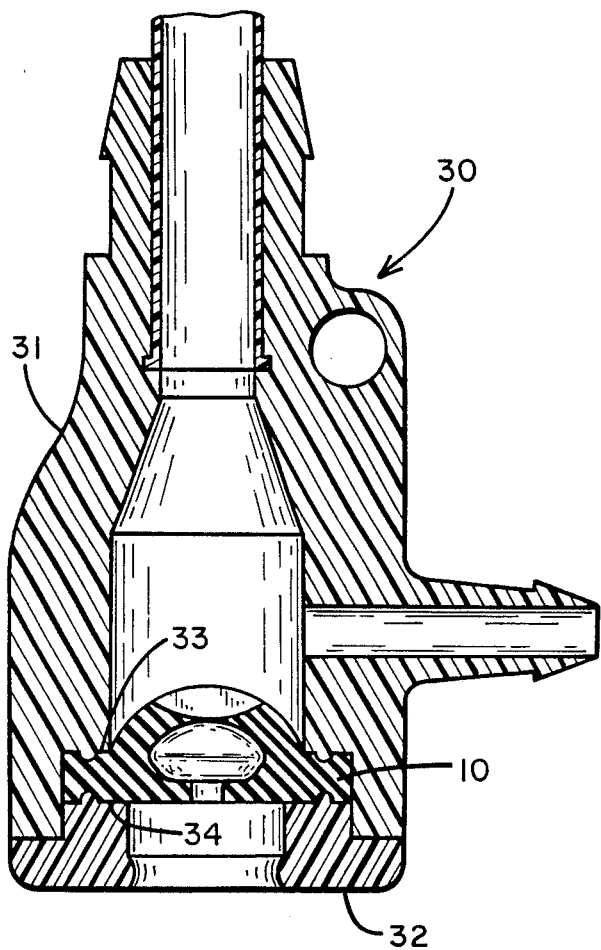
FIG. 6 is a plain view of the portion of an alternative introducer which retains the valve of the present invention.

As best shown in FIGS. 5 and 6, the introducer 20 includes an introduction tube 21 which is fixed to a receptacle assembly 22. The receptacle assembly 22 includes a union nut 23, a housing 24 having a chamber 25, a casing member 26, and a cover 27.

When assembled with the valve in place the valve is seated within the chamber 25 so that a tight seal is formed between the inner wall of chamber 25 and the outer perimeter of the valve's distal flange member 10. The casing member 26 is then inserted into the chamber 25 to maintain proper registration of the valve. Cover 27, which is reciprocally threaded with one end of the housing 24, is then screwed to the housing 24 to keep the valve and casing member 26 in place. Finally, the union nut, which is reciprocally threaded with the other end of housing 24, is screwed to the housing. When so assembled, the introducer has an internal lumen running through its length. This lumen is selectively sealed by the valve.

Figure 7:
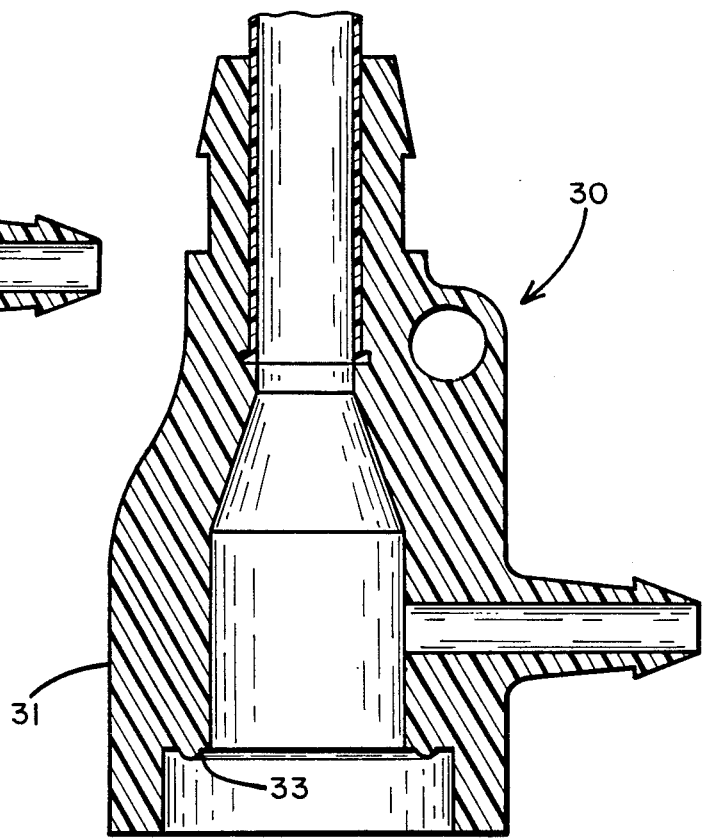
FIG. 7 is an exploded view of the assembly of FIG. 6.

FIGS. 6 and 7 show an alternative receptacle assembly 30 of an introducer. The receptacle assembly includes a housing 31 and a cover 32. Housing 31 and cover 32 each have a shelf (33 and 34 respectively) which are intended to cooperate to pinch the distal flange member 10 of the valve gasket about its periphery to hold the valve gasket in place. While a compression fit between the outer wall of cover 32 and the inner wall of housing 31 is generally sufficient to retain the parts in place, for additional safety, the cover and housing can be ultrasonically welded so they become fused together.

Once the introducer is assembled with the valve in place, a guide wire is then passed through the tubular hub of the introducer into opening 12 of distal section 10. The guide wire then traverses the hollow cavity 14 and is passed through the membrane initially covering the very narrow opening formed by the slit 13 and out of the valve. The entire design of the valve is directed toward keeping the valve closed until a guide wire or catheter is inserted through it. These same design features cause the valve gasket to clamp down under the force of the patient's blood pressure and form a tight seal about such implements. The material from which the valve is made causes the valve to be biased to a closed or sealing position. The design of the slit 13 enhances these natural tendencies. Finally, the configuration of the dome, its interval cavity and the slit, in conjunction with blood pressure, tends to collapse the dome about the penetrating guide wire to form a good, tight seal.

After the tip of the guide wire is advanced through the valve gasket, the guide wire is manipulated through the desired branching blood vessels until the treatment or testing site is reached. A catheter is then slipped over the guide wire through opening 12, across the hollow cavity 14 and through the slit 13. Again, the valve is biased towards a sealed position and the blood pressure will tend to collapse the dome about the penetrating catheter. After the working end of the catheter leaves the valve, it is also manipulated until the testing or treatment site is reached.

From a thorough reading of the above disclosure, those skilled in the art will understand that the present invention may be embodied in other specific forms without departing from its essential characteristics. Therefore, the above-described embodiment is not considered to be restrictive of the scope of the invention and, instead, in all respects, is only illustrative. All changes which come within the meaning and range of equivalency of the claims set forth are embraced within their scope.

What is claimed is:

1. A hemostasis valve gasket comprising:
   (a) a cylindrical base formed from a resilient material and having a central passage therethrough;
   (b) a dome-shaped member projecting outwardly from said base, said dome-shaped member having an internal hollow chamber in communication with said central passage of the cylindrical base; and
   (c) at least one arcuate slit formed in the external surface of said dome-shaped member and extending inwardly toward said hollow chamber to meet along a common tangent for forming a central, self-sealing passage between said internal chamber and said slit so that an implement can be passed through the central passage of the base, through the internal chamber and out through said self-sealing passage with said cylindrical base and said dome-shaped member forming a seal around said implement when it is present and to allow closure of the self-sealing passage when no implement is present.

2. The apparatus of claim 1 having a pair of accurate slits which intersect at right angles and are formed in the external surface of said dome shaped member.

3. The apparatus of claim 1 wherein said resilient material is natural rubber.

4. The apparatus of claim 1 wherein said resilient material is silicone rubber.

* * * * *